(12) United States Patent
Villani (10) Patent No.: US 7,335,174 B2
(45) Date of Patent: *Feb. 26, 2008

(54) CAPSULAR CONTRACTURE PREVENTING AND RELIEVING DEVICE

(76) Inventor: Maria Villani, 20311 SW. Acacia, Newport Beach, CA (US) 92660

( * ) Notice: Subject to any disclaimer, the term of this patent is extended or adjusted under 35 U.S.C. 154(b) by 137 days.

This patent is subject to a terminal disclaimer.

(21) Appl. No.: 11/111,086

(22) Filed: Apr. 20, 2005

(65) Prior Publication Data

US 2005/0251070 A1    Nov. 10, 2005

Related U.S. Application Data

(63) Continuation-in-part of application No. 10/400,023, filed on Mar. 25, 2003, now abandoned, which is a continuation of application No. 09/703,606, filed on Nov. 1, 2000, now Pat. No. 6,540,702.

(51) Int. Cl.
*A61H 7/00* (2006.01)
*A61H 19/00* (2006.01)
*A61B 17/00* (2006.01)

(52) U.S. Cl. ...................... 601/133; 606/201

(58) Field of Classification Search ............... 601/133, 601/134, 14, 148–152, 107; 604/74, 514; 606/129, 130, 201, 204; 602/19; 623/7; 450/18, 38, 45, 52–55

See application file for complete search history.

(56) References Cited

U.S. PATENT DOCUMENTS

| 146,805 | A |  | 1/1874 | Cox |
| 949,414 | A |  | 2/1910 | Cunningham |
| 990,279 | A |  | 4/1911 | Mayer |
| 1,795,073 | A |  | 3/1931 | Brown |
| 2,298,361 | A |  | 1/1942 | Freund |
| 2,598,003 | A |  | 5/1952 | Leo |
| 2,764,759 | A |  | 10/1956 | Gazelle |
| 3,326,218 | A |  | 6/1967 | McAlpine |
| 3,374,784 | A |  | 3/1968 | Brent et al. |
| 3,500,832 | A |  | 3/1970 | Nunnery |
| 4,202,343 | A |  | 5/1980 | Ichelson |
| 4,205,681 | A |  | 6/1980 | Nestor et al. |
| 4,249,534 | A | * | 2/1981 | Muldrow, Jr. ............... 606/201 |
| 4,580,561 | A | * | 4/1986 | Williamson ................. 606/130 |
| 4,662,356 | A | * | 5/1987 | Aronsohn .................... 606/201 |
| 5,050,595 | A |  | 9/1991 | Krafft |

(Continued)

*Primary Examiner*—Justine R. Yu
*Assistant Examiner*—Kristen C. Matter
(74) *Attorney, Agent, or Firm*—K&L Gates; Louis C. Cullman; Michelle S. Glasky (57) ABSTRACT

A device for exerting a compression force on a breast implant located within a user's breast. The device includes a support member adjustably connect to a compression member, the compression member comprising a positioning element on one side of the compression member such that the positioning element is aligned with medial side of the breast and a compression element on the second side of the compression member such that the compression element is positioned on lateral side of the breast, and means extending between the positioning element and the compressing element for retaining the positioning element and the compressing element on opposite sides of the breast, and means for providing pressure to the compressing element causing the compressing element to apply a compression force to the breast implant within the user's breast. Additionally a method for preventing capsular contracture after breast implant surgery is provided.

13 Claims, 6 Drawing Sheets

U.S. PATENT DOCUMENTS

| | | |
|---|---|---|
| 5,235,974 A | 8/1993 | Miller |
| 5,347,656 A | 9/1994 | Fabritz et al. |
| 5,998,693 A | 12/1999 | Zagame |
| 6,015,332 A | 1/2000 | Lee et al. |
| 6,027,396 A | 2/2000 | Yonchar |
| 6,540,702 B1 | 4/2003 | Sarango |

* cited by examiner

CAPSULAR CONTRACTURE PREVENTING AND RELIEVING DEVICE

RELATED APPLICATIONS

The present application is a continuation-in-part of U.S. patent application Ser. No. 10/400,023 filed on Mar. 25, 2003 now abandoned, which is a continuation of U.S. patent application Ser. No. 09/703,606 filed on Nov. 1, 2000, now U.S. Pat. No. 6,540,702 B1 issued on Apr. 1, 2004 entitled "Breast Compressing Device" the entire disclosures of which are incorporated herein by reference.

FIELD OF THE INVENTION

The present invention related generally to devices for preventing or relieving the effects of capsular contracture by compression of a breast implant after breast augmentation or reconstruction surgical procedures. More specifically, the present invention relates to a device which is able to provide safe and effective lateral compression forces to the breast implant in a controlled manner on either side of the breast.

BACKGROUND OF THE INVENTION

Capsular contracture is a common complication following breast reconstruction or augmentation when breast implants are placed into the body. After implantation, the body forms a lining around the implant. This lining is referred to as the "capsule," "tissue capsule" or "scar capsule". The formation of this capsule is a natural response and occurs in response to implantation of any foreign object, including, but not limited to: breast implants, pacemakers and artificial joints.

At the time of breast augmentation or breast reconstruction surgeries, tissues are injured and the body tries to repair the defect by generating new blood vessels at the site of the injury and secretes collagen to form a new tissue matrix. This scar tissue surrounds the breast implant in the form of a spherical capsule. All implants become encapsulated. The capsule is a living tissue that the body creates in response to the foreign object, the breast implant, and thus, undergoes dynamic changes.

Clinical studies with saline-filled implants demonstrate that in about 5 to 75% of patients, the capsule contracts, most often within 6 months of surgery. The shrinking of the capsule increases the pressure within the implant and is perceived as hardening of the implant by the patient. As time goes on, patients may experience significant discomfort, pain, distortion and displacement of the implant that may require additional surgeries. Capsular contracture may happen on one or both sides and with each additional surgery, the risk of developing capsular contracture increases. It is currently impossible to predict which patient with develop capsular contracture because of its multi-factorial nature. Development of capsular contracture is related to the surface properties of the implant, the position in which the implant is inserted, the surgical technique used during insertion, whether or not anti-microbial irrigation is used, the medical history of the patient, etc. Regardless of the cause, recurrence rates of capsular contracture are high and afflicted women often undergo multiple, and frequently ineffective, secondary surgical procedures.

In order to classify the capsular contracture, a system has been developed to compare the feeling and appearance of the breast after augmentation. This system, called the Baker Classification, is widely used by plastic surgeons:

Class I: the breast feels the same as a normal breast with no hardness or change in shape.

Class II: the breast is harder and although the implant is not yet visible, it can usually be felt.

Class III: the breast is firm and tender. The implant can be seen. The shape of the breast is usually distorted.

Class IV: the breast is hard and extremely painful. The shape of the breast is abnormal.

There are two currently available treatments for capsular contracture including closed capsulotomy and open capsulotomy. In closed capsulotomy, the surgeon forcibly squeezes the implant to "pop" the scar tissue (opening it up). Breast implant manufacturers do not recommend closed capsulotomy as it can lead to possible rupture of the implant.

There are two forms of open capsulotomy surgery. In the first type, the physician surgically breaks up the scar tissue in order to release the capsule's hold on the implant without removing the scar tissue. The second type of open capsulotomy involved the surgical removal of the scar capsule. Once the capsule is broken up or removed, however, the body will form a new capsule around the breast implant and this capsule is at high risk for contracture.

Manual compression of the breast after surgery can help prevent capsular contracture. By compressing the breast implant, the surface area of the capsule is increased and, with frequent compression, the capsule will not contract, thereby allowing the implant to retain its intended shape and the breast to have a normal appearance. For best results, the compression is recommended to be performed daily for several months after surgery. One disadvantage to manual compression is the level of force the patient is capable of producing is often not sufficient to prevent capsular contracture, is not linear with respect to time and cannot be adequately controlled for safety and effectiveness.

Therefore, a medical device is needed which provides patients who have received breast implants with controlled compression forces to the breast in order to prevent capsular contracture and its undesirable consequences.

SUMMARY OF THE INVENTION

The present invention provides a device to prevent or relieve capsular contracture following breast augmentation or breast reconstruction surgery. The device of the present invention provides safe and effective lateral compression forces to the breast implant in a controlled manner on either side of the breast thereby mechanically distorting the implant into a stretched ovoid shape and increasing its surface to volume ratio. This will stretch the periprosthetic scar tissue that is the source of capsular contracture. Such compression is expected to significantly reduce the risk of developing capsular contracture.

In an embodiment of the present invention, a capsular contracture preventing and relieving device is provided wherein the device comprises a support member adjustably connect to a compression member, the compression member having a first side and a second side, and the compression member comprising a positioning element on the first side of the compression member such that the positioning element is aligned with medial side of the breast, a compression element on the second side of the compression member such that the compression element is positioned on the lateral side of the breast, means extending between the positioning element and the compressing element for retaining the positioning element and the compressing element on opposite sides of the breast; and means for providing pressure to the compressing element causing the compressing element to apply a compression force to the breast implant.

In another embodiment of the present invention, the support member comprises a vertical solid support securely attached to a seat such than when a user is seated on the seat, the patient is positioned correctly for use of the breast implant compression device of the present invention. In yet another embodiment of the present invention, the support member is attached to a plurality of legs so that the support member stands on the floor.

In an embodiment of the present invention, the compression member is adjustably connected to the support member using a connection member wherein the connection member provides means to move the compression member vertically along the support member. The connection member further comprises pivoting means by which the compression member can be rotated 180 degrees.

In another embodiment of the present invention, the compression element comprises a compression pad connected to a piston adjustably connected to the compression member such that the compression element can be adjusted to align the compression member with the breast of the user.

In yet another embodiment of the present invention, the providing means is a control module including a pump and a supply line connecting the pump and the compressing element for providing air pressure therethrough. The control module includes means for determining an amount of pressure provided by the pump to the compressing element and means for adjusting the amount of pressure applied by the compressing element. In an embodiment of the present invention, the pump can be a mechanical, electromechanical, or electronically controlled pump.

In an embodiment of the present invention, the control module further includes means for adjusting a time period during which pressure is supplied to the compression element by the pump resulting in the compressing element producing compression and relaxation forces.

In another embodiment of the present invention, the control module further includes means for setting the number of compression cycles.

In an embodiment of the present invention, a method for preventing and relieving capsular contracture after breast implant surgery is provided comprising contacting a user's breast with the compression element of a breast implant compressing device, adjusting the compression element to the size and shape of the user's breast, applying pressure to the breast implants with the compression element in cycles of compression and rest.

In another embodiment of the present invention, the method for preventing capsular contracture after breast implant surgery comprises repeated cycles of compression and rest of approximately 5-15 seconds of compression and 5-15 seconds of rest.

DETAILED DESCRIPTION OF THE INVENTION

The present invention provides a device to prevent or relieve capsular contracture following breast augmentation or breast reconstruction surgery. The device of the present invention provides safe and effective lateral compression forces to the breast implant in a controlled manner on either side of the breast thereby mechanically distorting the implant into a stretched ovoid shape and increasing its surface to volume ratio. This will stretch the periprosthetic scar tissue that is the source of capsular contracture. Such compression is expected to significantly reduce the risk of developing capsular contracture.

Figure 1:
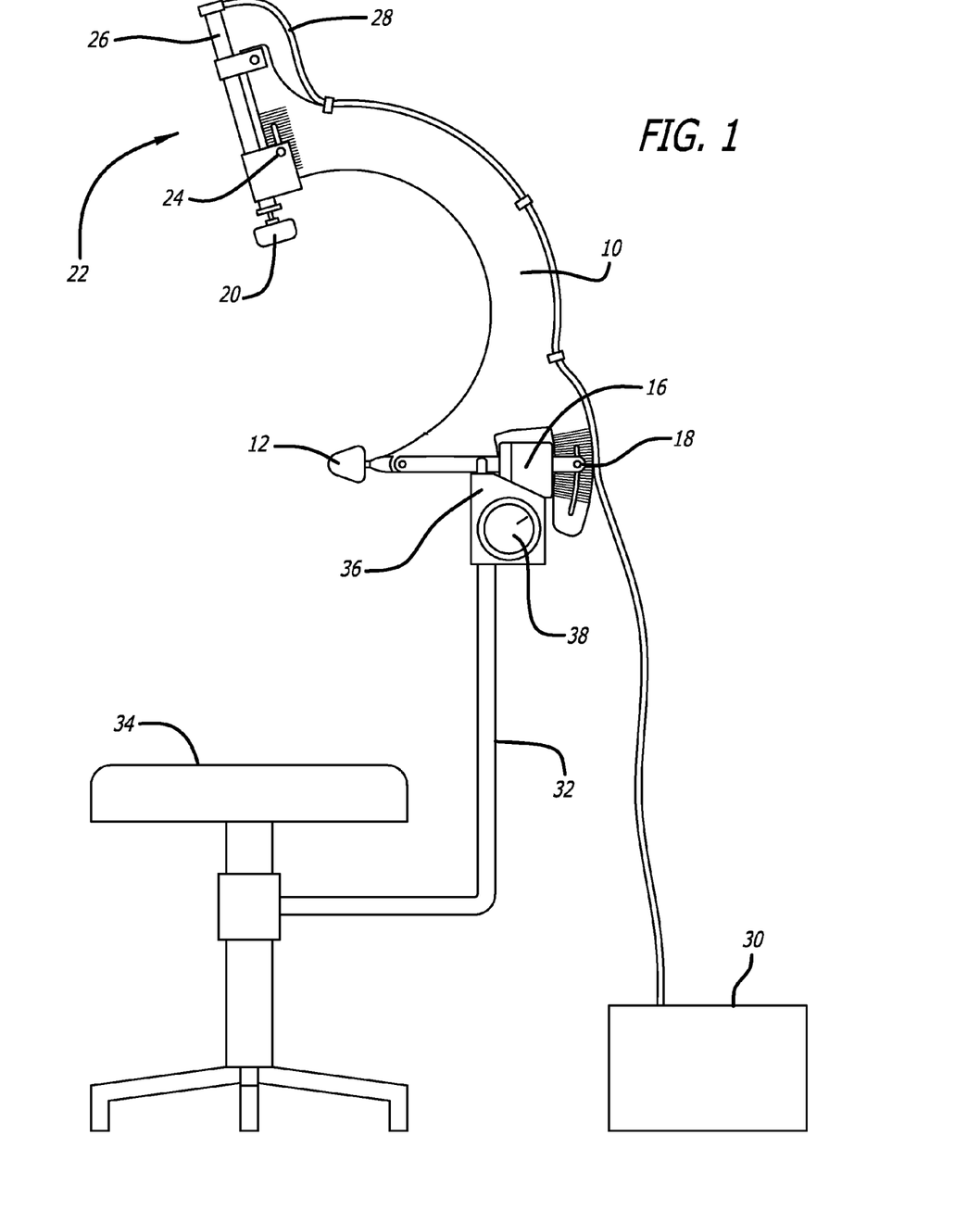
FIG. 1 depicts the capsular contracture preventing and relieving device of the present invention. In the embodiment of the device for preventing and relieving capsular contracture depicted in FIG. 1, the device for preventing and relieving capsular contracture is attached to a seat

Turning our attention now to the Figures, FIG. 1 depicts the capsular contracture preventing and relieving device of the present invention. The device comprises a compression member 10 pivotally and adjustably connected by a connection member 36 to a support member 32. Connection member 36 is adjustably attached to support member 32 such that connection member 32 moves vertically along the support member by adjusting knob 38. Connection member 36 is pivotally attached to compression member 10 by pivot joint 16. Pivot joint 16 allows compression member 10 to be rotated 180 degrees to accommodate compression of a breast implant in either breast. In the embodiment of the capsular contracture preventing and relieving device of the present invention depicted in FIG. 1, the support member 32 is attached to a seat 34. In another embodiment of the present invention, support member 32 attaches to a base unit which sits directly on the floor, without attaching to a seat.

Compression member 10 is additionally connected to a control module 30 through supply tubing 28. Control module 30 provides air pressure causing piston 26 to compress and retract at a constant pressure and rate. The breast is held in place by positioning element 12, compression member 10 and compression pad 20 and compressed through the action of piston 26 on compressing element 22.

Figure 2:
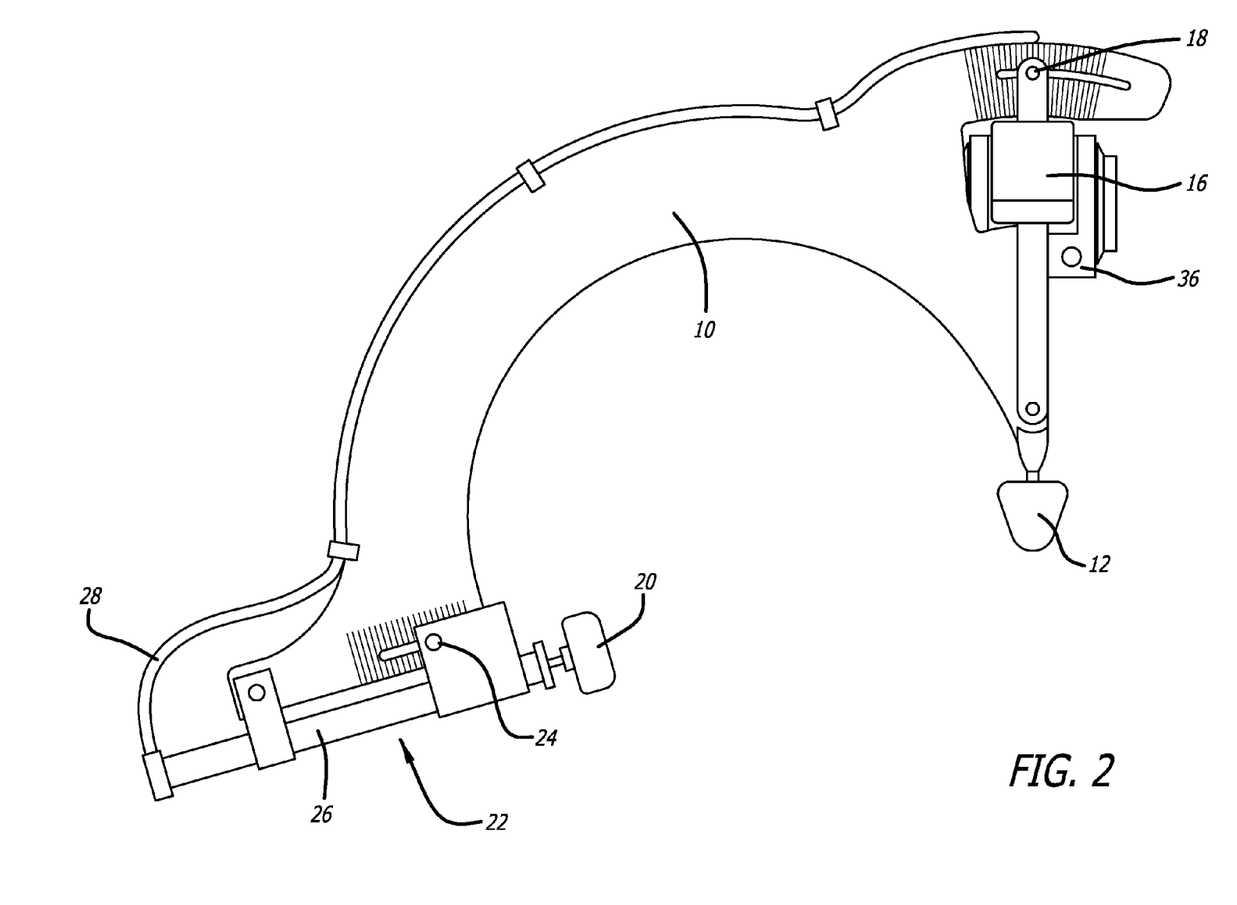
FIG. 2 depicts a top view of the compression member of the capsular contracture preventing and relieving device of the present invention.

FIG. 2 presents a top view of compression member 10. Compression member 10 comprises positioning element 12 which is placed between the user's breasts. Compression member 10 is designed such that when compression member 10 is placed against the user, compression element 22 is positioned on the lateral side of user's breast and positioning element 12 is positioned on the medial side of the same breast. Compression element 22 is comprised of piston 26 which is connected to supply line 28. Piston 26 is connected to compression pad 20 which provides the compression action upon the breast implant within the user's breast. The position of the compression element 10 relative to the user's breast is adjustable at locations 18 and 24 such that the capsular contracture preventing and relieving device is comfortably and securely positioned at the user's breast.

Figure 3:
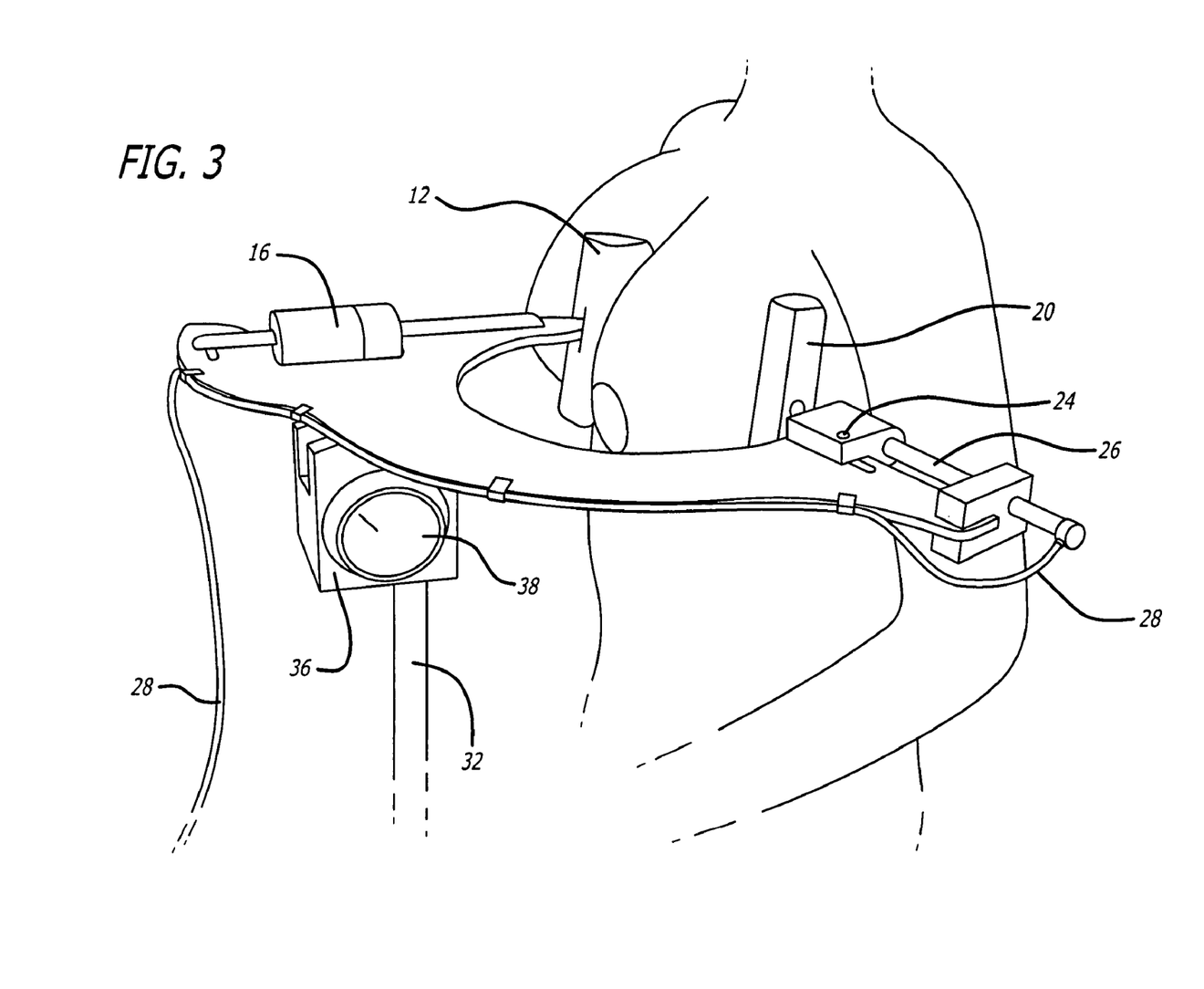
FIG. 3 depicts a side view of the capsular contracture preventing and relieving device of the present invention positioned on the body of a user.

The operation of the capsular contracture preventing and relieving device will now be described with references to the figures and specifically FIGS. 3, 4 and 5. In an embodiment of the present invention, a user in need of capsular contracture prevention and relief is seated on seat 34 and the capsular contracture preventing and relieving device of the present invention is brought in proximity to the user. The user must first remove any garments covering the upper body and expose the breast containing the implant to be compressed. Positioning element 12 is then centered between the user's breasts with compression element on the lateral side of the breast containing the implant to be compressed. The height of the compression member is adjusted vertically using knob 38 on connection member 36 such that the compression member 10 is situated even with the horizontal midpoint of the user's breasts. The position of compression member 10 is then adjusted at position 18 to rotate compression member 10 such that compression pad 20 is aligned with the lateral side of the user's breast. Compression element 22 is then adjusted at position 24 such that compression pad 20 is firmly pressed against the user's breast so that compression occurs at the base of the breast, the location of the breast implant, and thereby preventing the compression pad 20 from shifting between compression cycles. Thus the breast is snugly held between the positioning element 12 and the compression pad 20 (FIG. 3).

If compression is needed on implant within the user's second breast, compression member 10 is pivoted by lifting the lateral side of compression member 10 and rotating compression member 10 180 degrees such that compression member 10 is adjacent to the lateral side of the user's second breast and the adjustment steps repeated.

The adjustment of the capsular contracture preventing and relieving device to the user's breast is performed by a healthcare professional. In an embodiment of the present invention, a patient having completed breast implant surgery and in need of a capsular contracture prevention and relief would visit a healthcare professional and be fitted for the device. The adjustment settings are stored in microprocessor 60 and the device settings are not readjusted by the user.

Figure 4A:
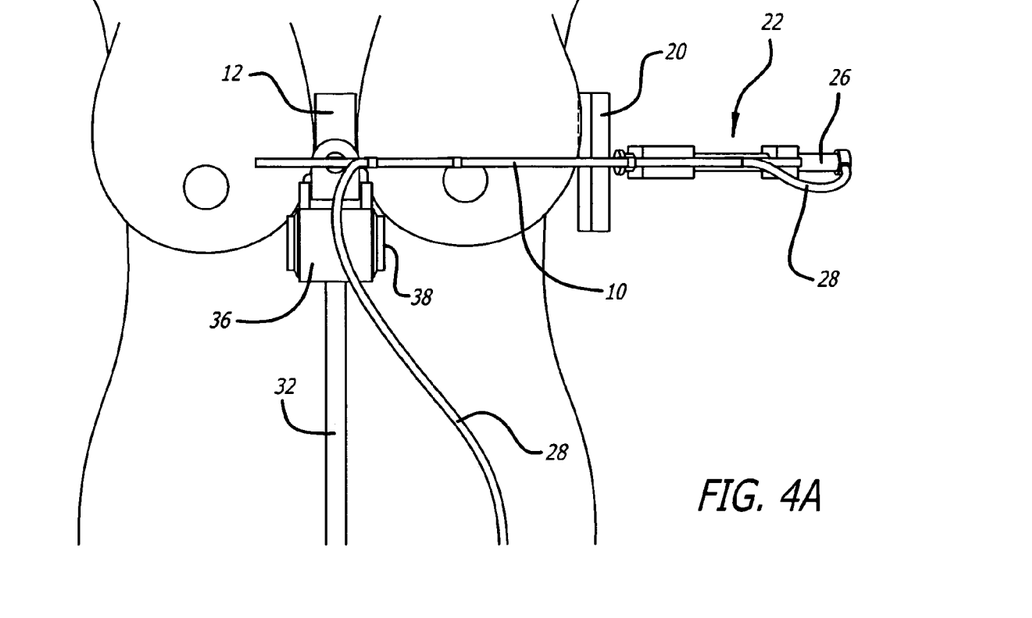
FIG. 4A-B depicts the capsular contracture preventing and relieving device of the present invention positioned on the left breast of a user in the resting position (FIG. 4A) and in the compressing position (FIG. 4B).
Figure 4B:
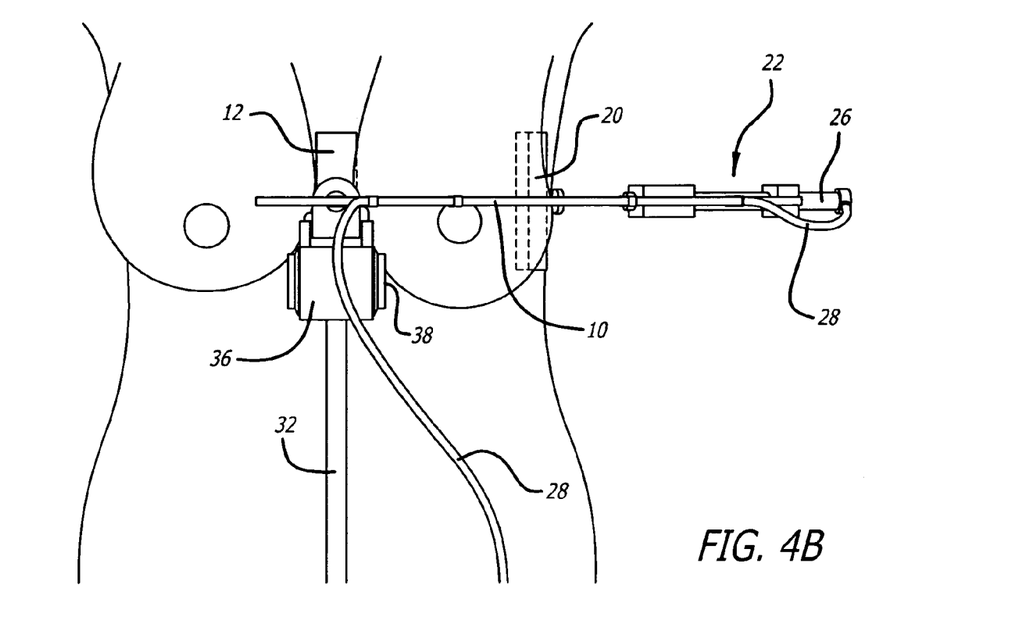
Figure 5A:
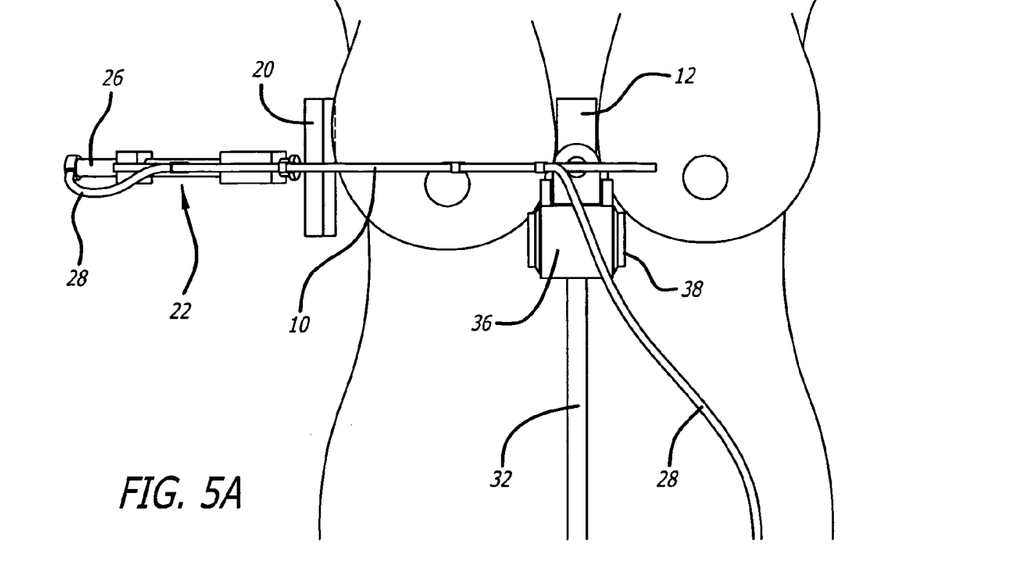
FIG. 5A-B depicts the capsular contracture preventing and relieving device of the present invention positioned on the right breast of a user in the resting position (FIG. 5A) and in the compressing position (FIG. 5B).
Figure 5B:
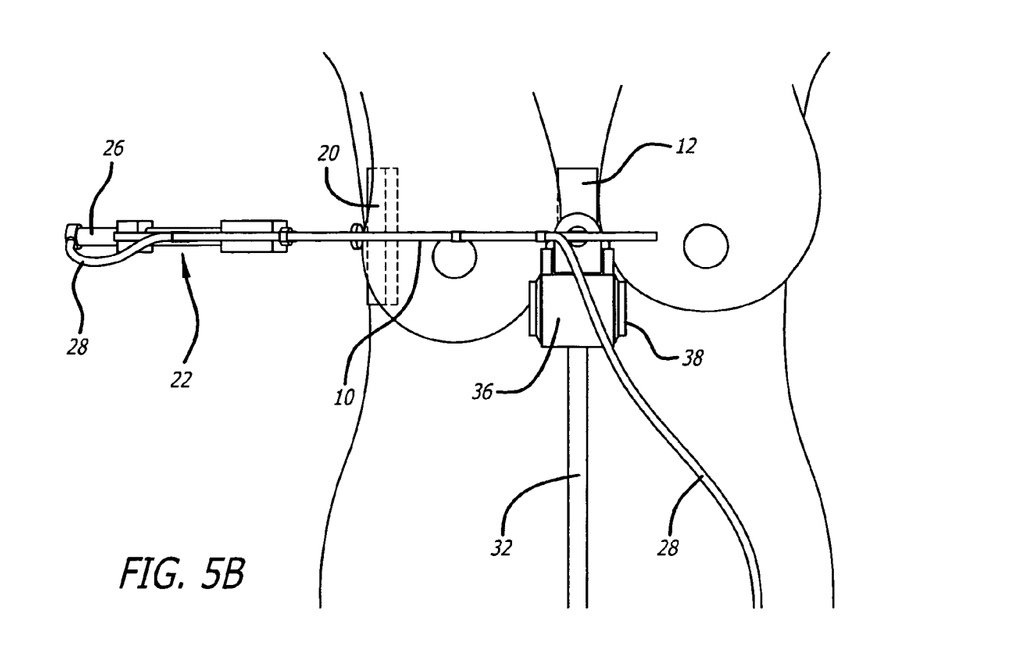

Once the compression member 10 has been adjusted for the user's breast, the compression cycle can begin (FIG. 4A). Pump 70 causes air pressure to flow through supply line 28 to piston 26 which then causes a force to be exerted on the lateral side of the breast by compression pad 20 (FIG. 4B). This causes the breast implant to be compressed. The force applied to the breast implant causes the implant to increase in surface area from a substantially spherical shape to an oval shape. The amount of pressure applied is indicated on the compression sensor 72. The compression sensor 72 monitors the pressure of piston 26. If the sensed pressure is greater than the pressure set by the user, the compression sensor transmits a control signal to microprocessor 60 causing microprocessor 60 to terminate the compression session. After the pressure has been applied for the time period set by the user, the pressure applied by piston 26 to the breast implant is removed. This pattern will repeat for the entire session time period as set by the user.

Compression cycles comprise approximately 5-15 seconds of compression followed by approximately 5-15 seconds of rest. Compression cycles are repeated for approximately 15 minutes per breast, or as recommended by a healthcare professional. The compression cycles are controlled by the control module 30.

Figure 6:
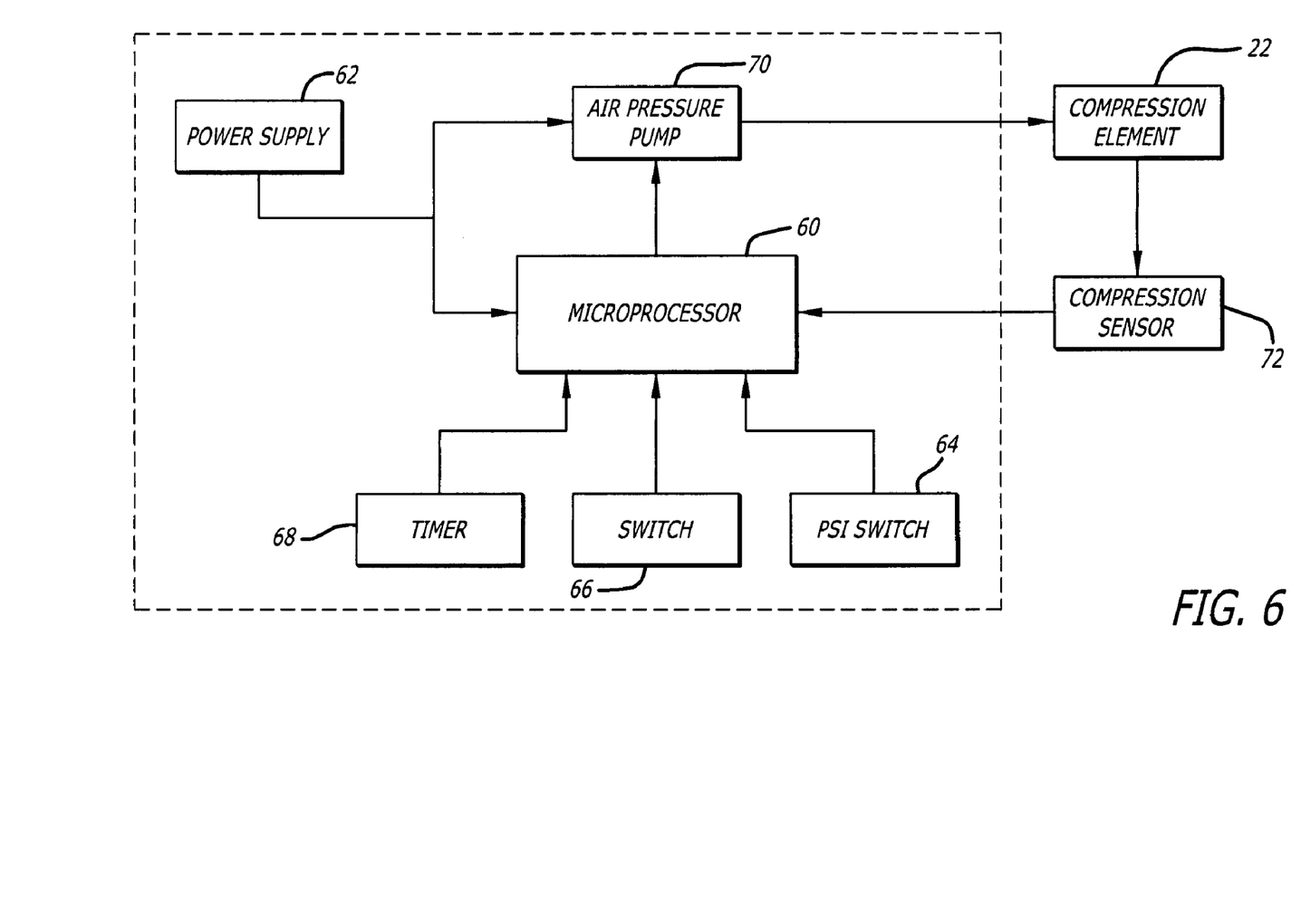
FIG. 6 is a block diagram of the control module of the capsular contracture preventing and relieving device of the present invention.

A block diagram illustrating the components of the control module 30 are shown in FIG. 6. As can be seen from this figure, control module 30 includes a microprocessor 60 for controlling the operation of the compression element 10. A power supply 62 is connected to the microprocessor 60 for supplying power to the control module 30. The switch 64 for selecting pressure to be applied (pounds per square inch, PSI) to a breast, the switch 66 for selecting the number of compressions (repetitions) and the timer 68 for setting the duration of a compression cycle are all connected to the microprocessor 60 for setting operating values within which the breast implant compressing device of the present invention will operate. Optionally, switches 64, 66 and 68 can be controlled by microprocessor 60. A pump 70 is connected to both microprocessor 60 and power supply 62 such that microprocessor 60 controls operation of pump 70 and the power supply 62 provides operating power for pump 70. Pump 70 is connected to the compression element 22 though supply tubing 28. Under the control of microprocessor 60, pump 70 is controlled to provide air pressure through supply tubing 28 to compression element 22 causing piston 26 to compress and retract. A compression sensor 72 is connected supply tubing 28 to measure the pressure applied by piston 26 and is connected to microprocessor 60 to terminate the action of pump 70 upon sensing that pressure applied by piston 26 is above a preset limit set by the user with switch 64 for selected the pressure to be applied. Microprocessor 60 causes the pump 70 to provide air pressure such that piston 26 compresses and retracts based upon the cycle time set by timer 68 for selecting the duration of a compression cycle and also continues to control pump 70 for a number of repetitions set by the user with switch 66 for setting the number of compression repetitions.

Microprocessor 60 additionally contains a data retrieval/memory storage device, such as, but not limited to a memory chip, such that the parameters of each use of the capsular contracture preventing and relieving device are recorded and are available for review by the appropriate healthcare worker. Microprocessor 60 is programmed with the user's individually-specified settings (such as height of the device, the position of compression element 22 and positioning element 12 and the amount of compression force) such that when the user intends to use the capsular contracture preventing and relieving device, the user-specified settings position the capsular contracture preventing and relieving device in the appropriate position for the user.

Upon completion of the session, the capsular contracture preventing and relieving device of the present invention is disengaged from the user and can be repositioned to compress the an implant within the second breast of the user in the manner described above (FIG. 5A-B) or stored away until the next compression session.

The compression element has a supply line whereby air pressure is introduced and the compressing element moves. Non-limiting examples of pressure sources include mechanical, electromechanical, or an electronic device having means for increasing and decreasing air pressure and having a pressure gauge whereby the user can monitor the pressure. A non-limiting example of a pressure source is a pump.

In a non-limiting embodiment of the present invention, patients will use the device up to several times per day beginning as soon as one week after surgery, or as recommended by a healthcare professional. In an exemplary embodiment, each session will last approximately 15 minutes for each breast implant with compression applied for approximately 10 seconds followed by 10 seconds of rest. Since most capsular contracture problems occur within six months of surgery, the capsular contracture preventing and relieving device of the present invention is used regularly during the first six months following surgery. In an embodiment of the present invention, a patient uses the capsular contracture preventing and relieving device for at least one time each date for up to one year after surgery. Additional treatment regimens are anticipated by the present invention based on individual health-care practitioner practice and are considered part of the present invention.

While certain embodiments of the capsular contracture preventing and relieving device of the current invention have been shown and described and disclosed in the appending claims, the invention is not intended to be limited to the details disclosed above, since it will be understood that various omissions, modifications, substitution and changes in the forms and details of the device illustrated and in its operation can be made by those skilled in the art without departing in any way from the spirit of the present invention.

Unless otherwise indicated, all numbers expressing quantities such as size, time, force and so forth used in the specification and claims are to be understood as being modified in all instances by the term "about." Accordingly, unless indicated to the contrary, the numerical parameters set forth in the following specification and attached claims are approximations that may vary depending upon the desired properties sought to be obtained by the present invention. At the very least, and not as an attempt to limit the application of the doctrine of equivalents to the scope of the claims, each numerical parameter should at least be construed in light of the number of reported significant digits and by applying ordinary rounding techniques. Notwithstanding that the numerical ranges and parameters setting forth the broad scope of the invention are approximations, the numerical values set forth in the specific examples are reported as precisely as possible. Any numerical value, however, inherently contains certain errors necessarily resulting from the standard deviation found in their respective testing measurements.

The terms "a" and "an" and "the" and similar referents used in the context of describing the invention (especially in the context of the following claims) are to be construed to cover both the singular and the plural, unless otherwise indicated herein or clearly contradicted by context. Recitation of ranges of values herein is merely intended to serve as a shorthand method of referring individually to each separate value falling within the range. Unless otherwise indicated herein, each individual value is incorporated into the specification as if it were individually recited herein. All methods described herein can be performed in any suitable order unless otherwise indicated herein or otherwise clearly contradicted by context. The use of any and all examples, or exemplary language (e.g. "such as") provided herein is intended merely to better illuminate the invention and does not pose a limitation on the scope of the invention otherwise claimed. No language in the specification should be construed as indicating any non-claimed element essential to the practice of the invention.

Groupings of alternative elements or embodiments of the invention disclosed herein are not to be construed as limitations. Each group member may be referred to and claimed individually or in any combination with other members of the group or other elements found herein. It is anticipated that one or more members of a group may be included in, or deleted from, a group for reasons of convenience and/or patentability. When any such inclusion or deletion occurs, the specification is herein deemed to contain the group as modified thus fulfilling the written description of all Markush groups used in the appended claims.

Preferred embodiments of this invention are described herein, including the best mode known to the inventors for carrying out the invention. Of course, variations on those preferred embodiments will become apparent to those of ordinary skill in the art upon reading the foregoing description. The inventor expects skilled artisans to employ such variations as appropriate, and the inventors intend for the invention to be practiced otherwise than specifically described herein. Accordingly, this invention includes all modifications and equivalents of the subject matter recited in the claims appended hereto as permitted by applicable law. Moreover, any combination of the above-described elements in all possible variations thereof is encompassed by the invention unless otherwise indicated herein or otherwise clearly contradicted by context.

Furthermore, numerous references have been made to patents and printed publications throughout this specification. Each of the above cited references and printed publications are herein individually incorporated by reference in their entirety.

In closing, it is to be understood that the embodiments of the invention disclosed herein are illustrative of the principles of the present invention. Other modifications that may be employed are within the scope of the invention. Thus, by way of example, but not of limitation, alternative configurations of the present invention may be utilized in accordance with the teachings herein. Accordingly, the present invention is not limited to that precisely as shown and described.

What is claimed is:

1. A capsular contracture preventing and relieving device comprising:
   a. a support member adjustably connected to a compression member;
   b. said compression member having a first side and a second side, and said compression member comprising a positioning element on said first side of said compression member such that said positioning element is adapted to be aligned with the medial side of a breast, compressing element on said second side of said compression member such that said compressing element is adapted to be positioned on lateral side of the same breast, and means extending between said positioning element and said compressing element for retaining said positioning element and said compressing element on opposite sides of said breast wherein said compressing element further comprises a compression pad connected to a piston adjustably connected to said compression member such that said compressing element can be adjusted for aligning the compression member with said breast of said user; and
   c. means for providing pressure to said compressing element for causing said compressing element to apply a compression force to a breast implant within said breast.

2. The device of claim 1 wherein said support member comprises a vertical solid support securely attached to a seat.

3. The device of claim 1 wherein said compression member is adjustably connected to said support member using a connection member.

4. The device of claim 3 wherein said connection member provides means to move said compression member vertically along said support member.

5. The device of claim 3 wherein said connection member further comprises pivoting means by which the compression member can be rotated 180 degrees.

6. The device of claim 1, where said means for providing pressure is a control module including a pump and a supply line connecting said pump and said compressing element for providing air pressure therethrough.

7. The device of claim 6, wherein said control module includes means for determining an amount of pressure provided by said pump to said compressing element.

8. The device of claim 7 wherein said means for determining an amount of pressure further comprises means for adjusting the amount of pressure applied by said compressing element.

9. The device of claim 6, wherein said control module further includes means for adjusting a time period during which pressure is supplied to said compression element by said pump resulting in said compressing element producing compression and relaxation forces.

10. The device of claim 6 wherein said control module further includes means to setting a number of compression cycles.

11. The device of claim 6 wherein said control module comprises a microprocessor.

12. The device of claim 6 wherein said control module further comprises a data retrieval/memory storage device.

13. The device of claim 6, wherein said pump is selected from the group consisting of mechanical, electro-mechanical, and electronically controlled pumps.

* * * * *